(12) United States Patent
Flaherty-Woods et al.

(10) Patent No.: US 10,376,198 B1
(45) Date of Patent: Aug. 13, 2019

(54) PILOT FATIGUE AND ATTENTION TUNNELING USING BIOMETRIC MONITORING

(71) Applicant: Rockwell Collins, Inc., Cedar Rapids, IA (US)

(72) Inventors: Emily M. Flaherty-Woods, Cedar Rapids, IA (US); Geoffrey A. Shapiro, Cedar Rapids, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 17 days.

(21) Appl. No.: 15/809,827

(22) Filed: Nov. 10, 2017

(51) Int. Cl.
*G06F 3/01* (2006.01)
*A61B 5/16* (2006.01)
*A61B 5/18* (2006.01)
*G08B 21/06* (2006.01)
*A61B 5/024* (2006.01)
*A61B 5/0205* (2006.01)

(52) U.S. Cl.
CPC .............. *A61B 5/168* (2013.01); *A61B 5/163* (2017.08); *A61B 5/18* (2013.01); *A61B 5/024* (2013.01); *A61B 5/0205* (2013.01); *G08B 21/06* (2013.01)

(58) Field of Classification Search
CPC ........ G08B 21/02; G08B 21/06; B60K 28/06; B60W 40/08; A61B 5/168; A61B 5/163; A61B 5/18; A61B 5/0205; A61B 5/024

USPC .......................................... 340/576, 575, 439
See application file for complete search history.

(56) References Cited

U.S. PATENT DOCUMENTS

2015/0360617 A1* 12/2015 Schulz .................... B60R 11/04 701/41
2017/0311831 A1* 11/2017 Freer .................. A61B 5/04014
2017/0337438 A1* 11/2017 el Kaliouby, Jr. ... A61B 5/0077

* cited by examiner

*Primary Examiner* — Munear T Akki
(74) *Attorney, Agent, or Firm* — Angel N. Gerdzhikov; Donna P. Suchy; Daniel M. Barbieri

(57) ABSTRACT

An on aircraft computer system records and analyzes biometric data to identify indicia of impaired performance, such as pilot fatigue, attention tunneling, or cognitive overload. Such impairment is identified by alterations in pilot gaze or eye movement, head movement, facial parameters, eye lid position, heart rate, breathing, or brain wave patterns. Appropriate corrective action is applied based on the type of impaired performance identified, including altering a level of automation, contacting a ground dispatcher or ground pilot, or contacting a co-pilot or other crew member. Biometric data is continuously logged and correlated with data from other avionics systems to refine formulas relating biometric data to states of alertness and crew rest procedures.

15 Claims, 2 Drawing Sheets

PILOT FATIGUE AND ATTENTION TUNNELING USING BIOMETRIC MONITORING

BACKGROUND

Pilots are subject to many factors that can impair performance, such as fatigue, cognitive overload, and attention tunneling. Fatigue is a common issue during both long and short haul flights, due to long operating hours, high and stressful workloads, jet lag, short turnaround times, and other factors. Fatigue reduces pilot alertness and reaction times, and results in failure to monitor flight critical information. The current approach to monitor pilot fatigue is based on best practices and self-assessment rather than independent measurement.

Attention tunneling is the involuntary fixation on an information source, which results in a pilot's failure to monitor other information sources. Attention tunneling can be attributed to high or unusual workload environments, automation induced complacency, display location, and other factors.

Cognitive overload refers to a pilot's inability to process a high volume of visual, auditory, cognitive, motor, speech, or tactile information. High workload driven by phase-of-flight requirements and pilot alertness, operational protocols, and poor human machine interface designs can adversely affect a pilot's cognitive processing of information.

Flight time and rest time are monitored, and fatigue mitigation strategies are implemented for long haul flights; however, there are no fatigue monitoring systems to actively monitor and detect pilot fatigue in real time, and substantially no strategies to combat attention tunneling and account for the cockpit's cognitive workload. Currently, break periods are specified as formulaic rules not adapting to pilots actual condition.

Consequently, it would be advantageous if a device existed that is suitable for biometrically monitoring pilots and co-pilots to identify fatigue, sub-optimal cognitive workload, and attention tunneling.

SUMMARY

In one aspect, embodiments of the inventive concepts disclosed herein are directed to an on aircraft computer system that records biometric data and analyzes such data for indicia of impaired performance, such as pilot fatigue, attention tunneling, or cognitive overload. Appropriate corrective action may be taken based on the type of impaired performance identified.

In a further aspect, biometric data is continuously logged and correlated with data from other avionics systems to refine formulas relating biometric data to states of alertness and crew rest procedures.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which.

DETAILED DESCRIPTION

Figure 1:
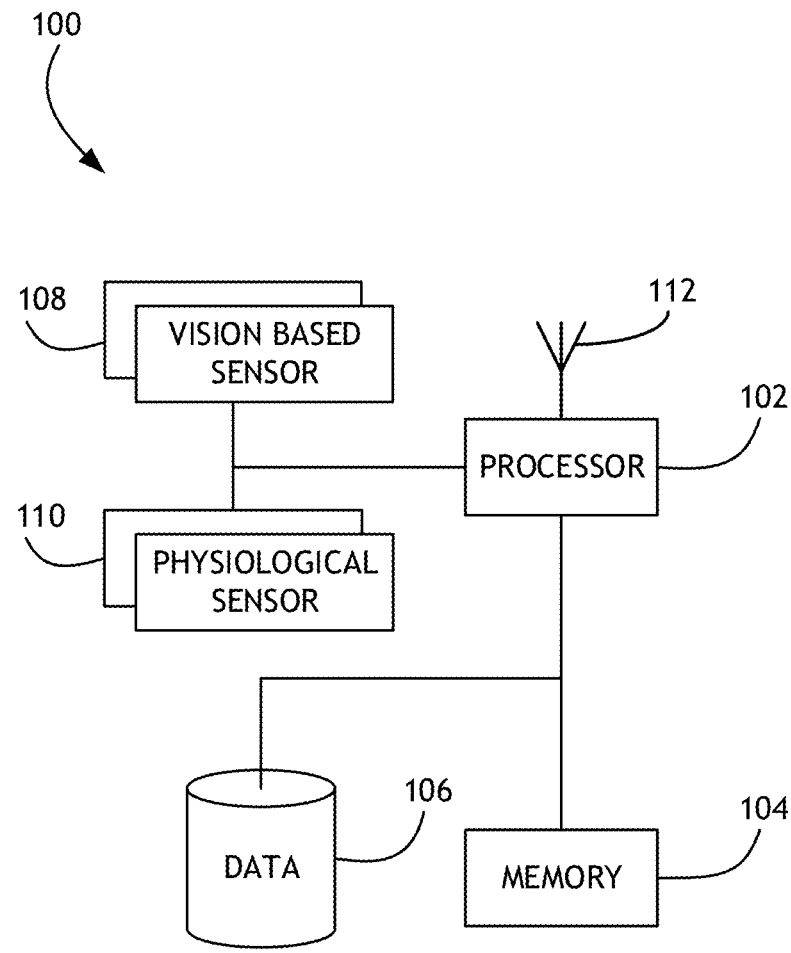
FIG. 1 shows a block diagram of a system suitable for implementing embodiments of the incentive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a' and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to an on aircraft computer system to monitor biometric data of the pilot and identify fatigue, attention tunneling, and cognitive overload. The computer system then initiates corrective action. Biometric data is logged to refine crew rest procedures.

Figure 2:
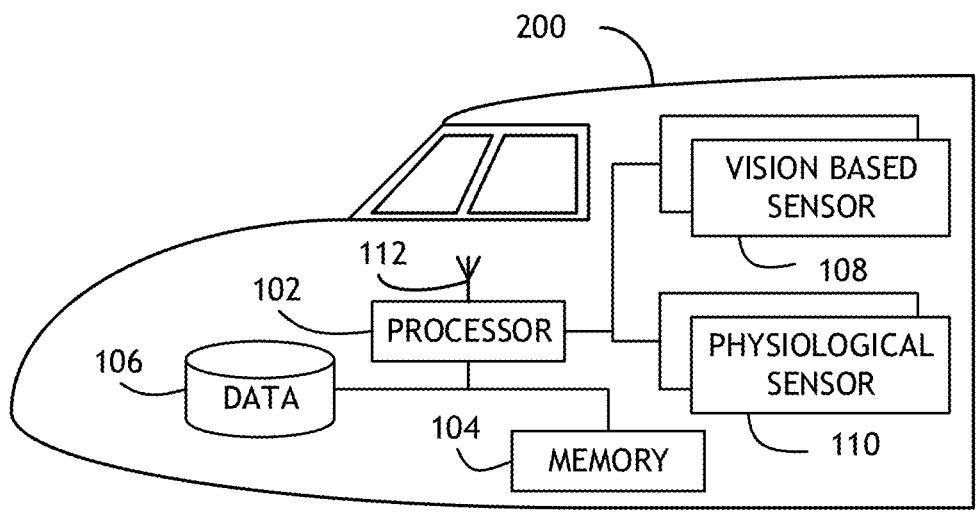
FIG. 2 shows a block environmental representation of a system suitable for implementing embodiments of the incentive concepts disclosed herein.

Referring to FIG. 1 and FIG. 2, a block diagram of a system 100 suitable for implementing embodiments of the incentive concepts disclosed herein, and a block environmental representation of an aircraft 200 including such system 100 are shown. The system 100 includes a processor 102, memory 104 in data communication with the processor 102 for storing processor executable code, a data storage device 106 in data communication with the processor 102 for storing biometric data and task or individual specific biometric profiles corresponding to idealized or otherwise acceptable biometric data that should be generated during a specific task, and one or more biometric data gathering devices 108, 110 for receiving biometric data about a pilot.

In at least one embodiment, the one or more biometric data gathering devices 108, 110 includes one or more vision based sensors 108; for example, a pilot facing camera or eye tracking sensor to record head and facial parameters, eye movement/gaze of the pilot and eye lid position. In at least one embodiment, the one or more biometric data gathering devices 108, 110 includes physiological sensors 110; for example, an electroencephalograph (EEG), an electrocardiograph (ECG or EKG), pulse sensor, or any other such biometric data sensing device.

In at least one embodiment, the system 100 includes a wireless communication device 112 in data communication with the processor 102. The wireless communication device 112 may be useful for sending or receiving biometric data, task or individual specific biometric profiles, or communicating a need for corrective action, such as to a ground controller.

In at least one embodiment, the processor executable code configures the processor 102 to receive biometric data from the one or more vision based sensors 108 and/or physiological sensors 110, and continuously log the biometric data in the data storage element 106. The processor executable code configures the processor 102 to analyze the biometric data to identify one or more indicia of impaired performance, potentially in comparison to stored biometric profiles. When indicia of impaired performance are identified, the processor executable code configures the processor 102 to initiate a corrective action as more fully described herein.

In at least one embodiment, the processor 102 transfers the stored biometric data and other correlated system and task data to an offline storage device for later analysis and correlation to historic data and other outside factors such as crew rest, crew sleet rhythms, flight schedules, etc. Such transfer may be in real time via the wireless communication device 112.

Figure 3:
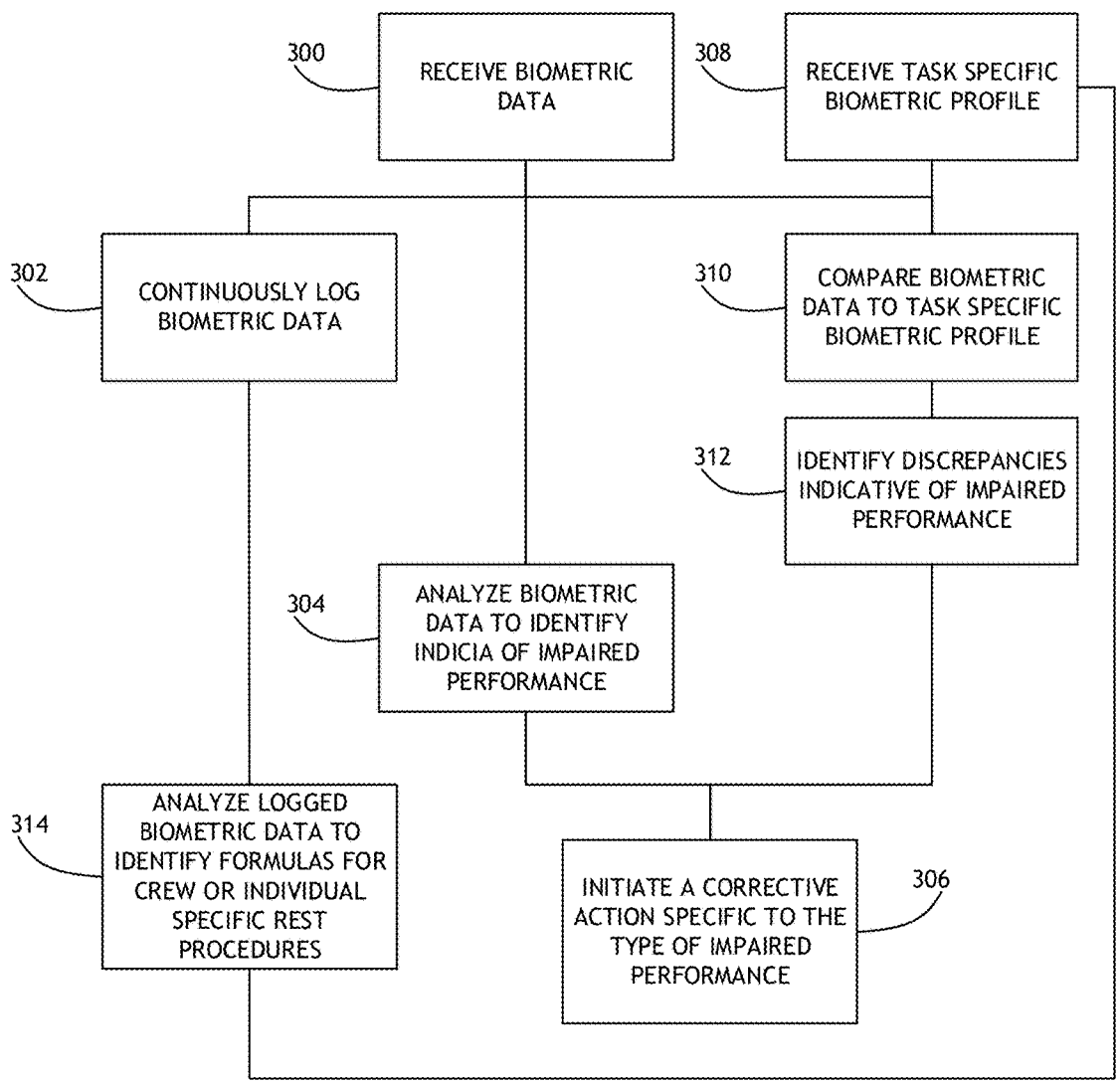
FIG. 3 shows a flowchart of an exemplary embodiment of the inventive concepts disclosed herein.

Referring to FIG. 3, a flowchart of an exemplary embodiment of the inventive concepts disclosed herein is shown. A computer system implementing embodiments of the inventive concepts disclosed herein receives 300 biometric data from one or more vision based sensors and/or physiological sensors. The biometric data is continuously logged 302 and correlated to a specific flight task or an individual duty schedule of the pilot.

In at least one embodiment, the biometric data is analyzed 304 to identify one or more indicia of impaired performance. Indicia of impaired performance may comprise data indicative of fatigue or attention tunneling such as characteristic heart rate, characteristic brain wave patterns, characteristic eye movement or lack of eye movement, eye lid position and blink rate, characteristic facial parameter changes or lack of facial parameter changes, or characteristic head movement or lack of head movement.

When indicia of impaired performance are identified, a corrective action may be initiated 306. In at least one embodiment, the corrective action is specific to the type of impaired performance identified. For example, in a highly automated environment, where pilot fatigue is identified, the level of aircraft automation may be altered; reduced to provide the pilot additional stimulus or increased to lower the cognitive workload. Alternatively, or in addition, a ground dispatcher or ground pilot may be automatically contacted to interact with the pilot to provide additional stimulus and evaluate the pilot's condition, or take over specific flight tasks from the ground to assist the pilot in the aircraft. Further, where additional rested crew members are available, a crew member, such as a co-pilot, may be automatically contacted to take over certain tasks from the pilot and alter the crew resource management (CRM).

In a situation where attention tunneling is identified, specific instrument cues may be utilized to redirect the pilot's attention. In at least one embodiment, such cues may be organized according to an idealized instrument observation pattern to facilitate the periodic observation of critical instruments. Attention capture techniques such as colors, symbology, blinking or flashing indicators, motion, haptic feedback, or sound may be used to disengage attention tunneling habits and shift the pilot's gaze toward information critical to the operational scenario. Where applicable, eye tracking may be used to determine exactly where the pilot's gaze is focused, and display warning messages at the identified location.

In a situation where cognitive overload is identified, a system may identify threats or critical information outside of the pilot's usual scan pattern and alert the pilot of that information. Further, the system may utilize context based filtering to declutter non-relevant display information based on the operational scenario, flight phase, and pilot workload level.

In at least one embodiment, the computer system also receives 308 a task or individual specific biometric profile including one more biometric reference points. Such biometric reference points may include recorded biometric data of experienced pilots during similar tasks or under similar situations; including recorded eye movement patterns and workload characteristics. Alternatively, or in addition, one or more biometric reference points may include biometric data of the specific pilot, recorded under ideal conditions. Further, the one more biometric reference points may comprise some combination of biometric data of experienced pilots, modified according to actual previously recoded biometric data of the specific pilot to produce a projected biometric profile for the specific pilot during a specific task.

The task or individual specific biometric profile is compared 310 to the biometric data to identify 312 discrepancies indicative of impaired performance, and a corrective action is initiated 306.

In at least one embodiment, logged biometric data is continuously or periodically analyzed 314 to establish or refine a function specific to the user, or flight crew including the user, relating active duty time, tasks, and biometric data to crew rest procedures. Neural network machine learning algorithms may be employed to refine the relationships between biometric data and indicia of impaired performance, and identify trends in airline operational deficiencies regarding pilot duty and fatigue patterns. Relevant data from other avionics systems may also be logged and correlated to the contemporaneous biometric data to provide context for the phase of flight and operational scenario. For example, data pertaining to specific aircraft or avionics tasks that are known or believed to induce high workload may be correlated to biometric data to provide system designers a means to gain insight into tasks that need to be streamlined.

In at least one embodiment, the task or individual specific biometric profile comprises a profile produced via analyzing the logged biometric data.

In at least one embodiment, the system continuously reports the pilot's alertness or operational status to a relevant monitoring agent such as a ground controller or ground pilot.

Embodiments of the inventive concepts disclosed herein are critical to enabling reduced crew or single pilot operations, and will provide independent measures necessary to facilitate reduced crew in the cockpit by providing a means to identify when crew members are unable to continue safe flight and notify relief crew or activate automation. Furthermore, a training application may utilize embodiments of the inventive concepts to compare the biometric data patterns of a pilot-in-training to previously characterized professional pilot biometric data patterns.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A computer apparatus comprising:
   at least one processor in data communication with a memory storing processor executable code;
   a data storage element in data communication with the at least one processor; and
   one or more biometric data recording devices in data communication with the at least one processor; wherein the processor executable code configures the at least one processor to: receive biometric data comprises an eye movement of a pilot from the one or more biometric data recording devices; continuously store the biometric data in the data storage element;
   analyze the biometric data to identify indicia of impaired performance including cognitive overload; analyze the stored biometric data over time to identify an individual specific correlation between time on duty and biometric data indicative of impaired performance during specific flight tasks and with respect to an individual duty schedule of the pilot; and initiate a corrective action.

2. The computer apparatus of claim 1, wherein:
   the processor executable code further configures the at least one processor to receive a biometric profile corresponding to desirable biometric data for a current task; and
   analyzing the biometric data to identify indicia of impaired performance comprises comparing the biometric data to the biometric profile to identify discrepancies characteristic of cognitive overload.

3. The computer apparatus of claim 2, wherein:
   the one or more biometric data recording devices comprises at least one vision based sensors; and
   comparing the biometric data to the biometric profile comprises comparing an eye movement pattern of a pilot to a stored eye movement pattern of an expert pilot.

4. The computer apparatus of claim 1, wherein:
   the one or more biometric data recording devices comprises at least one vision based sensors; and
   analyzing the biometric data to identify indicia of impaired performance comprises identifying a lack of eye movement over time indicative of attention tunneling.

5. The computer apparatus of claim 1, wherein the corrective action further comprises identifying a rested crew member and calling the rested crew member to a cockpit.

6. The computer apparatus of claim 1, wherein the processor executable code further configures the at least one processor to periodically report a biometrically determined alertness level of a pilot to a ground controller.

7. A method comprising:
   receiving biometric data from one or more biometric data recording devices in an aircraft cockpit, including at least one vision based sensors;
   continuously storing the biometric data;
   receiving a biometric profile corresponding to desirable biometric data for a current task;
   analyzing the biometric data to identify indicia of impaired performance including cognitive overload by comparing the biometric data to the biometric profile to identify discrepancies in a pilot's actual eye movement as compared to a stored eye movement pattern in the biometric profile;
   analyzing the stored biometric data over time to identify an individual specific correlation between time on duty and biometric data indicative of impaired performance during specific flight tasks and with respect to an individual duty schedule of the pilot; and
   initiating a corrective action.

8. The method of claim 7, wherein the biometric profile comprises an eye movement pattern derived via the analysis of the stored biometric data.

9. The method of claim 7, further comprising:
   correlating the biometric data to historic data of at least one of crew rest, crew sleep rhythms, and flight schedules.

10. An aircraft comprising: computer system comprising: at least one processor in data communication with a memory storing processor executable code; a data storage element in data communication with the at least one processor; and one or more biometric data recording devices in data communication with the at least one processor; wherein the processor executable code configures the at least one processor to: receive biometric data comprises an eye movement of a pilot from the one or more biometric data recording devices; continuously store the biometric data in the data storage element; analyze the biometric data to identify indicia of impaired performance; analyze the stored biometric data over time to identify an individual specific correlation between time on duty and biometric data indicative of impaired performance during specific flight tasks and with respect to an individual duty schedule of the pilot; and initiate a corrective action comprising reducing a level of automation to provide a stimulus to the pilot.

11. The aircraft of claim 10, wherein:

the processor executable code further configures the at least one processor to receive a biometric profile corresponding to desirable biometric data for a current task; and analyzing the biometric data to identify indicia of impaired performance comprises comparing the biometric data to the biometric profile to identify discrepancies characteristic of pilot fatigue.

12. The aircraft of claim 11, wherein: the one or more biometric data recording devices comprises at least one vision based sensors; and comparing the biometric data to the biometric profile comprises comparing an eye movement pattern of the pilot to a stored eye movement pattern of an expert pilot.

13. The aircraft of claim 10, wherein:

the one or more biometric data recording devices comprises at least one vision based sensors; and analyzing the biometric data to identify indicia of impaired performance comprises identifying a lack of eye movement over time indicative of attention tunneling.

14. The aircraft of claim 10, wherein the corrective action comprises identifying a rested crew member and calling the rested crew member to a cockpit.

15. The aircraft of claim 10, wherein the processor executable code further configures the at least one processor to periodically report a biometrically determined alertness level of the pilot to a ground controller.

* * * * *